United States Patent [19]

Knudson et al.

[11] Patent Number: 4,549,951

[45] Date of Patent: Oct. 29, 1985

[54] ION SELECTIVE ELECTRODE

[75] Inventors: Mark B. Knudson, Arden Hills; Walter L. Sembrowich; Vinodhini Guruswamy, both of Shoreview, all of Minn.

[73] Assignee: SenTech Medical Corporation, Arden Hills, Minn.

[21] Appl. No.: 649,434

[22] Filed: Sep. 11, 1984

[51] Int. Cl.[4] .............................................. G01N 27/46
[52] U.S. Cl. .................................... 204/416; 204/418; 427/58; 427/299
[58] Field of Search ....................... 204/416, 418, 419; 427/58, 299

[56] References Cited

U.S. PATENT DOCUMENTS

| 3,406,109 | 10/1968 | Molloy | 204/415 |
|---|---|---|---|
| 3,562,129 | 2/1971 | Simon | 204/195 |
| 3,700,576 | 10/1972 | Bloch et al. | 204/418 |
| 3,892,833 | 7/1975 | Hattori et al. | 204/419 |
| 3,957,607 | 5/1976 | Simon et al. | 204/180 |
| 4,021,325 | 5/1977 | Pungor et al. | 204/419 |
| 4,116,796 | 9/1978 | Havas et al. | 204/419 |
| 4,133,735 | 1/1979 | Afromowitz et al. | 204/195 |
| 4,182,667 | 1/1980 | Dobson et al. | 204/416 |
| 4,214,968 | 7/1980 | Battaglia et al. | 204/195 |
| 4,225,410 | 9/1980 | Pace | 204/412 |
| 4,250,010 | 2/1981 | Kondo et al. | 204/412 |
| 4,276,141 | 6/1981 | Hawkins | 204/418 |
| 4,340,457 | 7/1982 | Kater | 204/195 |
| 4,388,167 | 6/1983 | Ono et al. | 204/419 |

FOREIGN PATENT DOCUMENTS 0898314  1/1982  U.S.S.R. ............... 204/418

OTHER PUBLICATIONS

Trojanowicz et al., "A Potassium-Selective Electrode with Solid Internal Contact", *Talanta*, vol. 29, No. 2, (1982), pp. 113-117.

Cattral and Frieser, *Anal. Chem.*, 43:1905, (1971).

T. Stoworzewicz et al., at The Symposium on Ion-Selective Electrodes in Mutrafured, Hungary, Oct. 1972, (Proceedings reported in *Ion-Selective Electrodes*), pp. 259-267.

Cheek, Wales and Nowak, PH Response of Platinum and Vitreous Carbon Electrodes Modified by Electropolymerized Films, *Anal. Chem.*, vol. 55, pp. 380-381, (1980).

Freiser, "Coated Wire Ion-Selective Electrodes," *Ion-Selective Electrodes in Analytical Chemistry*, vol. 2, pp. 85-105, (1980).

Moody and Thomas, "Poly (Vinyl Chloride) Matrix Membrane Ion-Selective Electrodes," *Ion-Selective Electrodes in Analytical Chemistry*, vol. 1, pp. 287-308, (1978).

*Ion-Selective Electrodes in Analytical Chemistry*, vol. 1, H. Freiser, Editor, pp. 173-177.

*Ion-Selective Electrode Methodology*, Covington, vol. 1, pp. 155-172, (1979).

"The New Kodak Analyzer", Ektachem 700 is Here, *Clinical Chemistry*, Jul. 25, 1983.

*Primary Examiner*—T. Tung
*Attorney, Agent, or Firm*—Kinney & Lange

[57] ABSTRACT

An ion selective electrode includes a conductive electrode body which is supported by an insulating substrate. A convex dome-shaped membrane containing an electroactive species is deposited over and is directly in contact with the electrode body and a surface of the substrate surrounding the electrode body. The membrane has its greatest height above the electrode body and slopes down to meet the surface of the substrate. A moat formed in the insulating substrate surrounds the space from the electrode body to define the outer boundary of the dome-shaped member.

22 Claims, 11 Drawing Figures

ION SELECTIVE ELECTRODE

REFERENCE TO COPENDING APPLICATIONS

Reference is made to the following copending applications which are assigned to the same assignee as the present application: Ser. No. 550,360, filed Nov. 10, 1983 entitled "Clinical Chemistry Analyzer" by M. Knudson and W. Sembrowich; Ser. No. 550,361, filed Nov. 10, 1983 entitled "Multiple Species Group Disposable Sensing Device for Clinical Chemistry Analyzer" by M. Knudson, W. Sembrowich and S. Carlson; Ser. No. 550,313, filed Nov. 10, 1983 entitled "Disposable Single-Use Sensing Device for Clinical Chemistry Analyzer" by R. Little and R. Laska; and Ser. No. 598,868, filed Apr. 11, 1984, entitled "Self-Calibrating Single-Use Sensing Device for Clinical Chemistry Analyzer" by R. Baker and R. Funk.

BACKGROUND OF THE INVENTION

1. Field of the Invention

The present invention relates to devices for sensing the presence of specific ions in fluids. In particular, the present invention relates to ion selective electrode (ISE) technology, and methods of making ion selective electrodes.

2. Description of the Prior Art

An ion-selective electrode (ISE) is an electrode which exhibits an electrical response which is a function of concentration of a specific ion contained in a solution which is in contact with the ISE and a reference electrode. Ion selective electrodes operate on the basis of the Nernst principle, which was discovered by W. H. Nernst, a German physicist, in the late 1800's. The Nernst equation defines a logarithmic relationship between the potential of a solution and its ionic concentration. When an ion selective electrode and a reference electrode are exposed to a solution, a potentiometric measurement can be made between the two electrodes which indicate the concentration in the solution of the particular ion to which the ion selective electrode responds.

The Nernst equation can be written as:

$$Y = M \log_{10} X + B$$

where X is ion concentration, Y is the output potential, M is the Nernstian slope, and B is a constant.

Most commercially available ion selective electrodes include an internal reference electrode, an electrolyte (in either liquid or gel form) which is in contact with the internal reference electrode, and a membrane which separates the internal reference electrode and the electrolyte from the solution. The membrane is commonly a glass or polymeric membrane in which an electroactive species is incorporated. The particular electroactive species differs depending upon the particular ion to be sensed.

Coated wire electrodes are a type of ion selective electrode in which an electroactive species is incorporated in a thin polymeric film coated directly to a metallic conductor. Coated wire electrodes differ from other ion selective electrodes in that they do not use an electrolyte as an internal reference solution. Although coated wire electrodes offer simplified construction in contrast to other ion selective electrodes, they have not found significant use other than in experimental studies.

Although ion selective electrode (ISE) technology has been known for several decades, its use generally has been limited to laboratories with highly trained technicians making the measurements and interpreting the data. One of the deterrents to the use of ISE systems outside the laboratory has been the necessity for calibration of electrodes to establish their Nernstian slopes (M) in terms of the millivolt output response (Y) of the electrode per decade change in concentration (X). After this is done, a further measurement has to be made in the test solution to assess its concentration. From time to time, the ISE has to be recalibrated since the Nernstian slope can change by several millivolts and its intercept on the Y axis (i.e. the constant B) can shift.

Still another deterrent is that when ISE's are initially put into use or reused after storage, they need to be equilibrated in a suitable solution. This "preconditioning" of an ISE is time-consuming and inconvenient.

In the past, ISE's have typically exhibited significant drift. One of the major causes of this drift in ISE's is capacitive effects which are uncontrolled and therefore "float". This floating or changing capacitance causes drift, error, and the need for standardization and restandardization. The capacitance effects are related to three significant deficiencies in the prior art ion selective electrodes.

First, the spatial relationship of the reference electrode to the sensing electrode is not fixed.

Second, the prior art ISE's typically are constructed in multiple layers over a conductor, and each of these layers have varying characteristics which give varying capacitances and therefore uncontrollable changes in capacitance.

Third, in certain multilayer ISEs having a hydrophylic layer interposed between the sensing electrode and the conducting layer, the capacitance changes continuously with time as the dried hydrophyllic layer changes its state of hydration during the test. There are still other types of electrodes which have various layers are not fixed; and these can be physically deformed as well, causing additional uncontrollable changes in capacitance.

SUMMARY OF THE INVENTION

The present invention is an improved ion selective electrode which provides an essentially instantaneous response with no need for initial equilibrium time, and which exhibits a fixed slope. The electrode of the present invention has a simple structure which does away with the need for an internal electrolyte associated with an internal reference electrode.

The ion selective electrode of the present invention includes a conductive electrode body which is supported by an insulating substrate. A convex dome-shaped membrane containing an electroactive species is deposited over and is directly in contact with the electrode body and a surface of the substrate surrounding the electrode body. The membrane has its greatest height above the electrode body and slopes down to meet the surface of the substrate.

The electrode body has a surface area A1 which is less than the area A2 of the membrane. In preferred embodiments, the ratio A1/A2 is preferably in a range of about 0.01 to about 0.25. The height of the membrane over the electrode body is preferably greater than about 0.5 mm.

In preferred embodiments of the present invention, the insulating substrate includes a moat which surrounds and is spaced from the electrode body. An inner edge of the moat defines an outer boundary of the dome-shaped membrane.

The present invention does not include an electrolyte or a separate internal reference. This greatly simplifies both the structure and the fabrication of the electrode, and eliminates multiple layers which are a cause of drift in prior art ISE's. With the present invention, ISE's having Nernstian slopes which are highly reproducible can be manufactured on a large scale basis.

DETAILED DESCRIPTION OF THE PREFERRED EMBODIMENTS

Figure 1A:
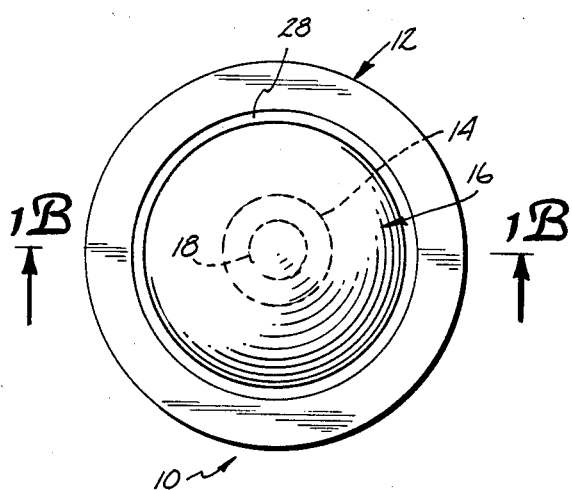
FIGS. 1A and 1B are top and cross-sectional views of a preferred embodiment of the ion selective electrode of the present invention.
Figure 1B:
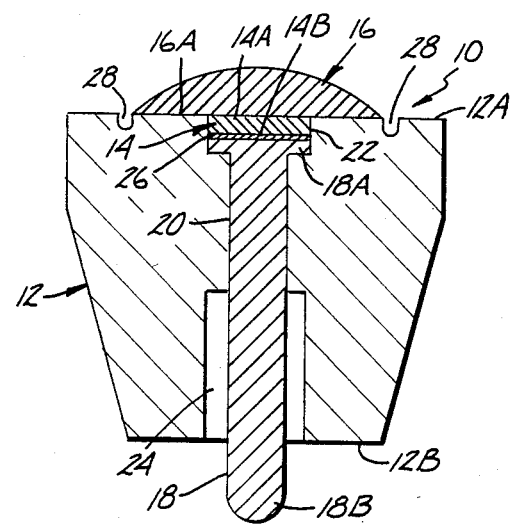

In FIGS. 1A and 1B, a preferred embodiment of the ion selective electrode 10 of the present invention is shown. In this embodiment, ISE 10 is formed by insulating substrate 12, conductive electrode body 14, species selective membrane 16, and conductive pin 18.

Substrate 12 is, in this preferred embodiment, an insulating plastic body having a top surface 12A and a bottom surface 12B which are generally planar. Extending through substrate 12 is hole 20, with an enlarged upper recess 22 at its upper end and an enlarged lower recess 24 at its lower end. Pin 18 has its head 18A positioned in upper recess 22 and extends downward through hole 20 so that lower end 18B is exposed below lower surface 12B.

Electrode body 14 is inserted in upper recess 22 so that top surface 14A is coplanar with surface 12A. Bottom surface 14B is bonded to conducive pin 18 by conductive silver epoxy 26.

Surrounding and spaced from electrode body 14 is annular moat 28, which is a groove formed in upper surface 12A of substrate 12. In the embodiment shown in FIGS. 1A and 1B, moat 28 and electrode body 14 are concentrically arranged.

Membrane 16 is preferably formed by a mixture of a polymer dispersed in plasticizer with an electroactive species dispersed therein. As shown in FIG. 1B, membrane 16 has a convex dome shape, with its greatest height over electrode body 14. Inner surface 16A of membrane 16 covers and is in direct contact with top surface 14A of electrode body 14, as well as the portions of top surface 12A of substrate 12 which are located within moat 28. The outer periphery of membrane 16 is defined by the inner shoulder of moat 28.

Conductive pin 18 provides an electrical conductive path by which electrode body 14 can be connected to electrical measurement equipment necessary to make a potentiometric measurement based upon the potential difference between ISE 10 and another electrode (e.g. a reference electrode) which does not interact with the specific ion of interest in the same manner as ISE 10.

ISE 10 of the present invention exhibits instantaneous response and a predictable Nernstian slope to within ±2 millivolts (and usually within ±1 millivolt). This makes the present invention well suited for use in a disposable, single-use sensing device like the ones described in the above-mentioned copending applications. As a result of the highly reproducible slope, and the instantaneous response without the need for preconditioning or for equilibration, ISE 10 permits the use of a one point calibration technique like that described in the previously mentioned copending application Ser. No. 596,868 entitled "Self-Calibrating Single-Use Sensing Device for Clinical Chemistry Analyzer" by R. Baker and R. Funk. In other words, with ISE 10 is it only necessary for a single calibration measurement to be made, with a known concentration, since slope M is a single known value and the calibrant concentration X1 is known. By measuring the voltage output Y1, a value for constant B is determined. A second measurement with a sample of unknown concentration yields output Y2 from which the unknown concentration value X2 can be calculated, since both slope M and constant B are known.

The extreme simplicity of construction of the present invention contributes to its suitability for use in a disposable, single-use sensing device. Unlike prior art devices, the present invention does not utilize a complex geometry or multiple layers which increase manufacturing complexity and cost, and contribute to drift and unpredictable slope values.

In preferred embodiments of the present invention, substrate 12 is made of acetonitrile butadriene styrene (ABS), and electrode body 14 is a carbon cylinder cut from a carbon (graphite) rod. Although other conductive materials (such as metals like platinum) have also been used as electrode body 14, carbon is a preferred electrode body material because it works best with a wide range of different electroactive compounds. This is particularly important since membrane 16 is in direct contact with top surface 14A of electrode body 14.

Prior to the deposition of membrane 16, top surfaces 14A and 12A are cleaned with methanol. Polishing of top surfaces 14A prior to cleaning also appears to be advantageous, although not absolutely necessary. It has been found that the more uniform and finer grained the surface 14A of electrode body 14, the less variation in the value of constant B of the Nernst equation. Coarse sanding of the surface 14A results in variation of about ±100 millivolts in the value of constant B. With the use of finer grade abrasives, the variation is reduced to about ±40 millivolts.

The alignment of the crystalline structure of electrode body 14 at surface 14A is believed to play a role in response characteristics of ISE 10. The mobility of electrons is highest when the diamond structure of graphite, for example, is perpendicular to the direction of electron flow. Electrode body 14 is typically cut from an extended graphite rod, and most of the crystals of body 14 are aligned in the direction for optimum electron flow. Some polishing, therefore, appears to be of advantage in giving a more uniform Gibbs free energy at the surface. However, polishing which alters the crystalline structure at surface 14A appears to reduce electron transfer, and therefore response, and also increases variation in the value of constant B.

The present invention lends itself to a simplified manufacturing process, since only a single deposition is required for each ISE. After surfaces 14A and 12A have been cleaned, the membrane material, in liquid form, is deposited on surface 14A. The liquid naturally forms the dome-shaped structure due to surface tension, which holds the liquid material within the boundaries defined by moat 28.

ISE 10 of the present invention is useful as an ion sensor for a wide range of different ions. The structure remains the same, regardless of the particular electroactive species which is incorporated within membrane 16. For purposes of illustration, the following examples describe a number of different membrane compositions, all of which have been used successfully with the ISE structure of the present invention.

In each example, substrate 12 was ABS plastic, electrode body 14 was a carbon (graphite) disc of 2.032 mm diameter, and conductive pin 18 was copper. Moat 28 had an inner diameter of 3.048 mm.

EXAMPLE NO. 1

A potassium ion ISE in accordance with the present invention used a membrane which incorporated valinomycin as the electroactive species. The membrane composition was made up of 0.0088 grams of valinomycin in 0.0221 grams of high molecular weight polyvinyl chloride (PVC) with 0.1995 grams of didecylpthalate which acted as a plasticizer in approximately 0.35 milliliters of tetrahydrafuran.

EXAMPLE NO. 2

A sodium ion ISE was fabricated using the monocyclic antibiotic monensin as the electroactive species. The membrane composition was identical to that used in the potassium ion ISE described in Example No. 1, with the ionophore valinomycin being replaced weight-for-weight by monensin.

EXAMPLE NO. 3

To eliminate the effect of pH dependence, the acid group in monensin was substituted with a methyl group, and the resulting methyl monensin was used as the electroactive species in the membrane. The weight of the plasticizer in the membrane was reduced considerably to 0.09 grams. All other components were the same as in Example Nos. 1 and 2, with methyl monensin substituted for monensin weight-for-weight.

EXAMPLE NO. 4

Sodium ion ISEs using the sodium ionophore N-N dibenzyl-N-N diphenyl 1-2 phenelenedioxydiacetamide were also studied. In this example, 0.005 grams of the ionophore was mixed with high molecular weight polyvinyl chloride of 0.0086 grams together with 0.0860 grams of didecylpthalate and made up in 0.350 milliliters of tetahydrafuran.

EXAMPLE NO. 5

A hydrogen ion (pH) selective electrode formed in accordance with the present invention used tridodecylamine as the electroactive compound. The membrane mixture was similar to Example No. 1, with tridodecylamine replacing valinomycin weight-for-weight.

EXAMPLE NO. 6

A chloride ion ISE used Aliquat 336 (which consists mainly of triepryl-methylammonium chloride) as the electroactive compound. 0.6630 grams of Aliquat 336 was dissolved in 0.5 milliliters of decyl alcohol. 0.08 grams of cellulose acetate was dissolved in 1 milliliter of cyclohexanone separately. When both of these mixtures had been homogenized, the cellulose acetate mixture was added to the Aliquat mixture and the resulting mixture was then vortexed rapidly to form a uniform homogenous membrane mixture. This mixture was then deposited on the previously prepared electrode/substrate surface.

The electrode responses for the ISEs of Example Nos. 1-6 were monitored as a function of concentration by using the ISE together with a silver/silver chloride reference electrode (from Orion Research, Inc.) and measuring the signal between the two electrodes obtained in four different solutions using an Orion pH meter. The solutions were made up for testing in the physiological concentrate ranges found in whole blood, and the ionic strength of the solutions were maintained with suitable salts. Except as otherwise stated, the concentration of the four solutions used to test the electrode response were multicomponent mixtures with a fixed ionic strength of 160. The ionic contents of the four solutions were as follows:

|  | Solution I | Solution II | Solution III | Solution IV |
| --- | --- | --- | --- | --- |
| Na+ | 0.75 | 100 | 125 | 160 |
| K+ | 1.5 | 3.0 | 6.0 | 10.0 |
| Cl− | 70 | 90 | 116 | 152 |
| pH | 7.784 | 7.53 | 7.014 | 6.877 |

The ionic strength of these solutions is made up by adding appropriate amounts of $MgCl$ and $MgSO_4$. The pH was maintained by adding sodium TES and hydrogen TES in suitable porportions.

Figure 2:
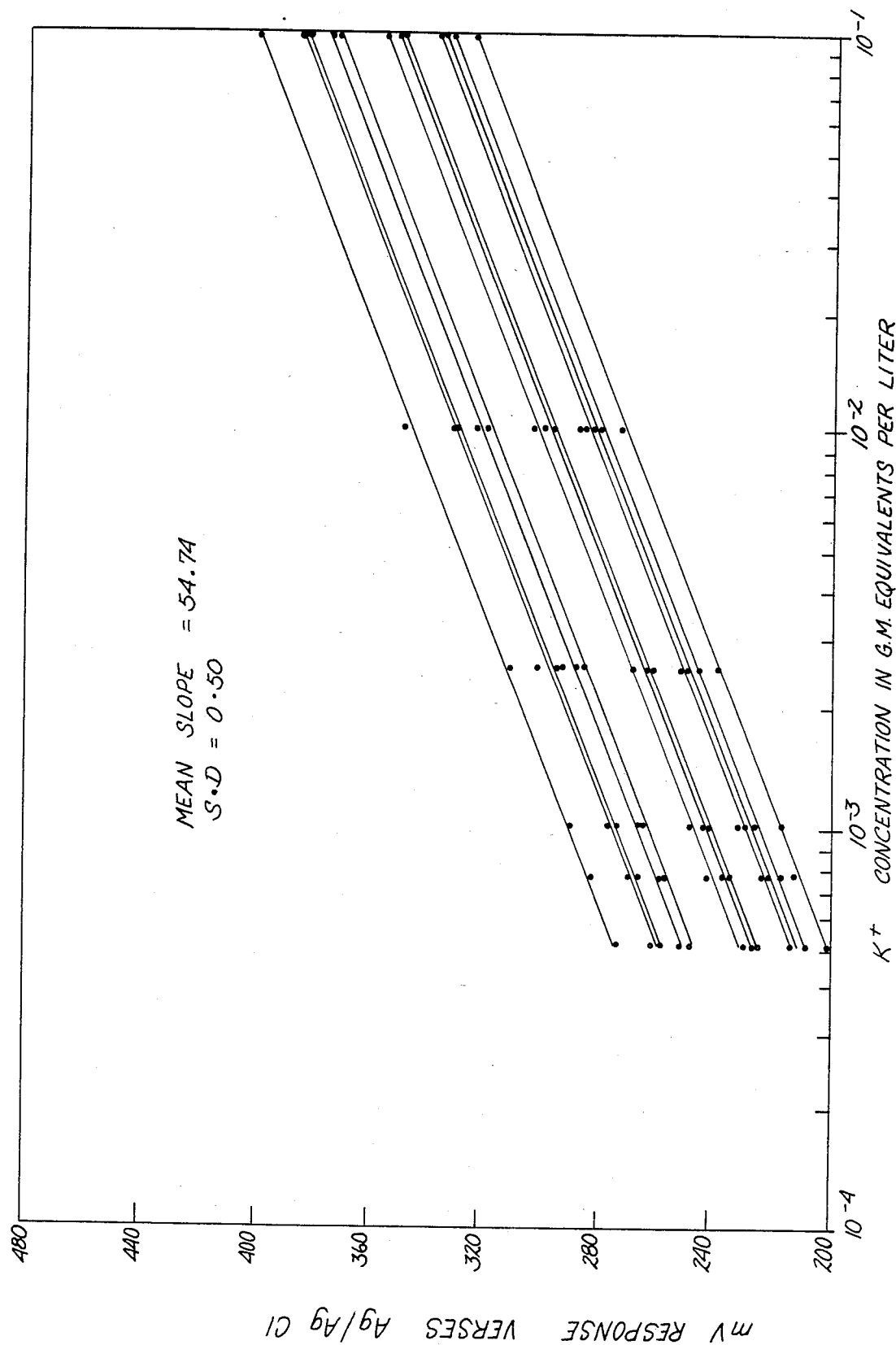
FIG. 2 is a graph showing the response of ISEs of the present invention having a valinomycin incorporated membrane to potassium in 0.1N NaCl solution.

As shown in FIG. 2, the response of valinomycin incorporated membrane ISE's (Example 1) was linear with a slope of about 54 millivolts per decade of concentration change. The standard deviation of slope observed was ±0.5 millivolts.

Figure 3:
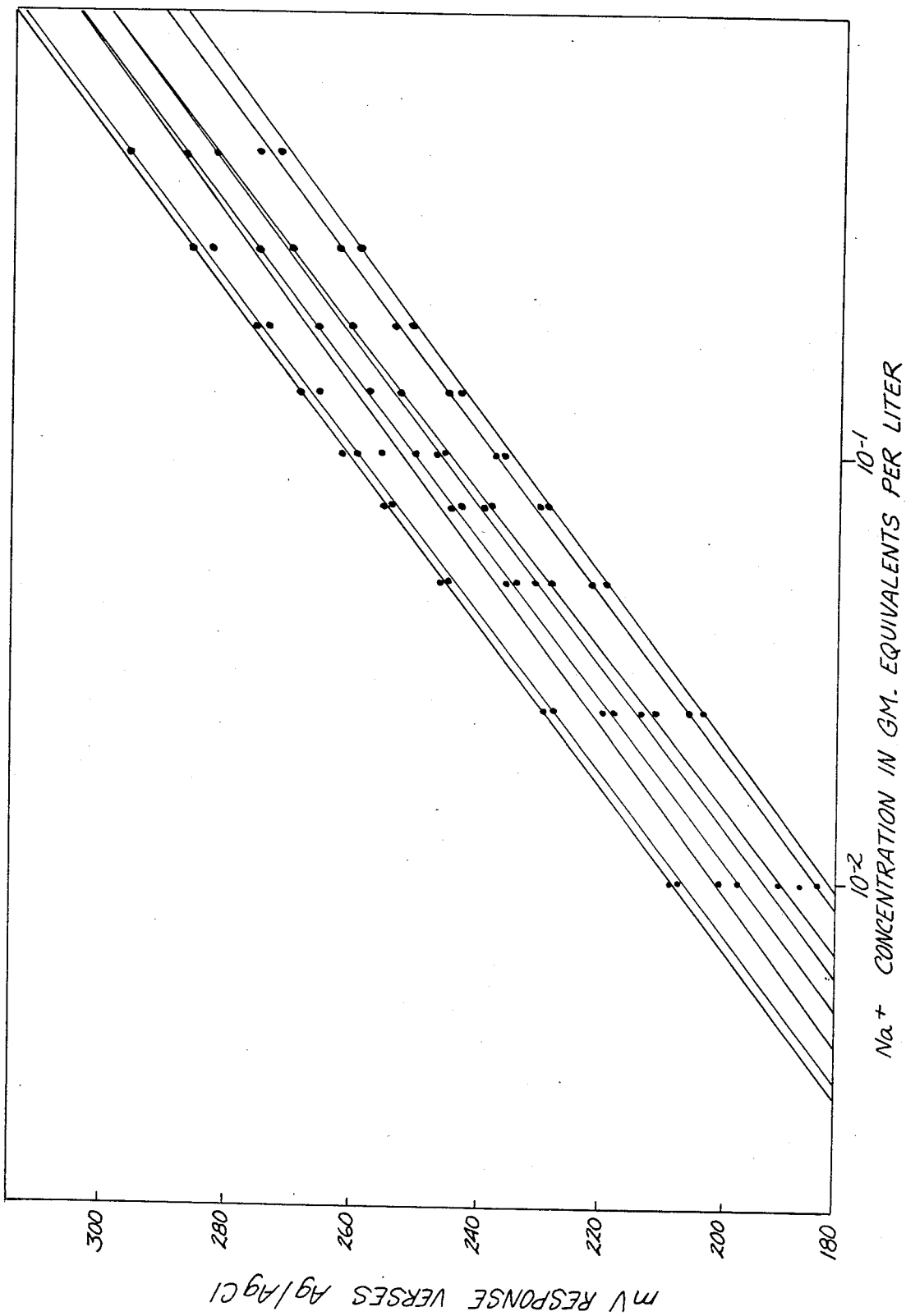
FIG. 3 is a graph showing the response of ISEs of the present invention having a monensin incorporated membrane to sodium in NaCl solution.

ISEs using a monensin incorporated membrane (Example 2) exhibited excellent linearity in response to sodium concentration, as shown in FIG. 3. Because of the known sensitivity of monensin to potassium, the potassium level in the reference solutions used for testing were reduced to approximately 10 meq. The selectivity of sodium over potassium under those conditions was excellent. It was found, however, that the ISEs of Example 2 were pH sensitive due to the acid group in monensin.

Figure 4:
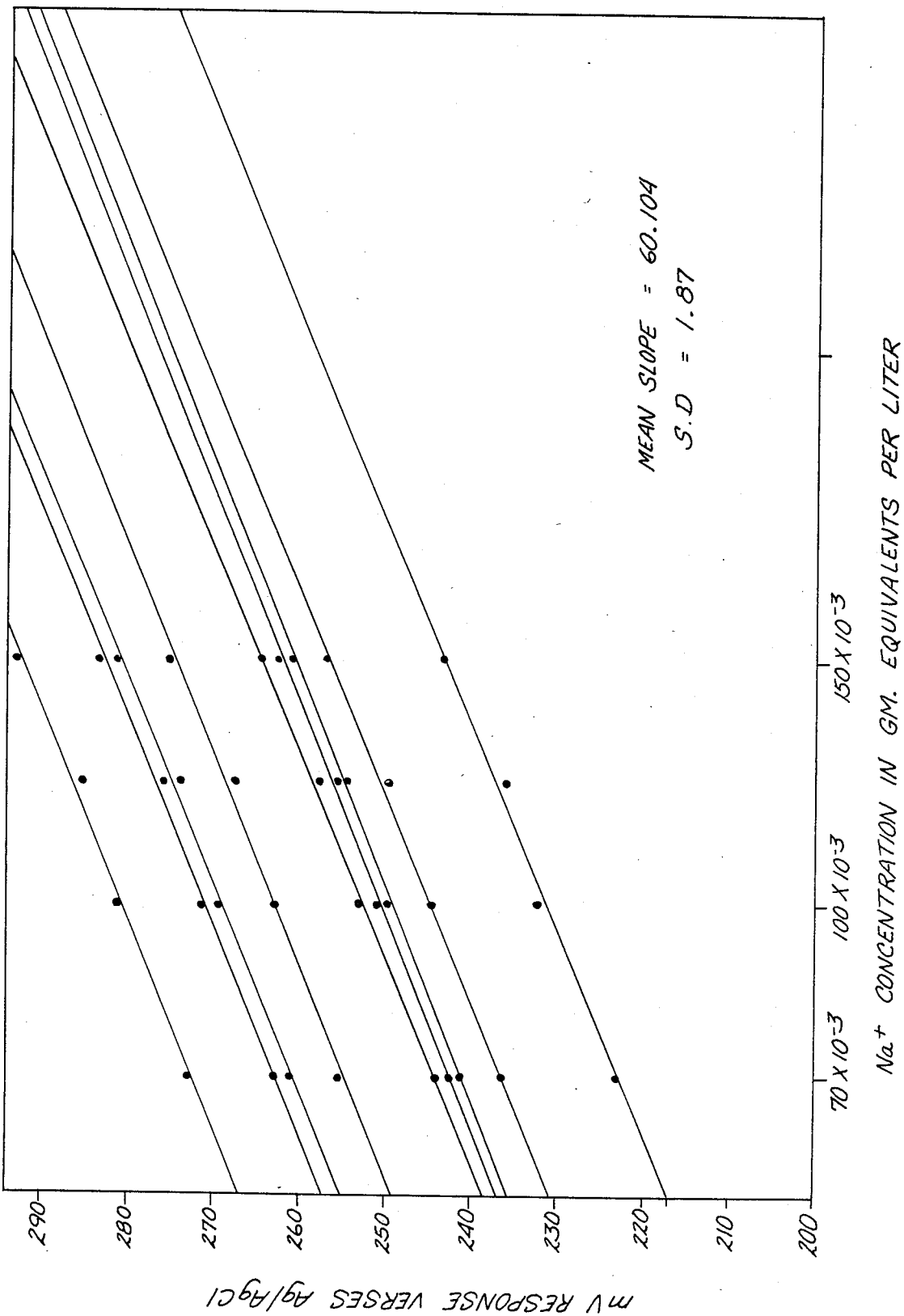
FIG. 4 is a graph showing the response of ISEs of the present invention having a methyl monensin incorporated membrane to Na+ ions in the physiological range of blood.

As shown in FIG. 4, the ISEs using methyl monensin incorporated membranes (Example 3) exhibited a Nernstian slope with excellent linearity and reproducibility. The selectivity of the methyl monensin incorporated membrane ISEs over potassium, magnesium and hydrogen ions was found to be excellent in the physiological range for blood.

Figure 5:
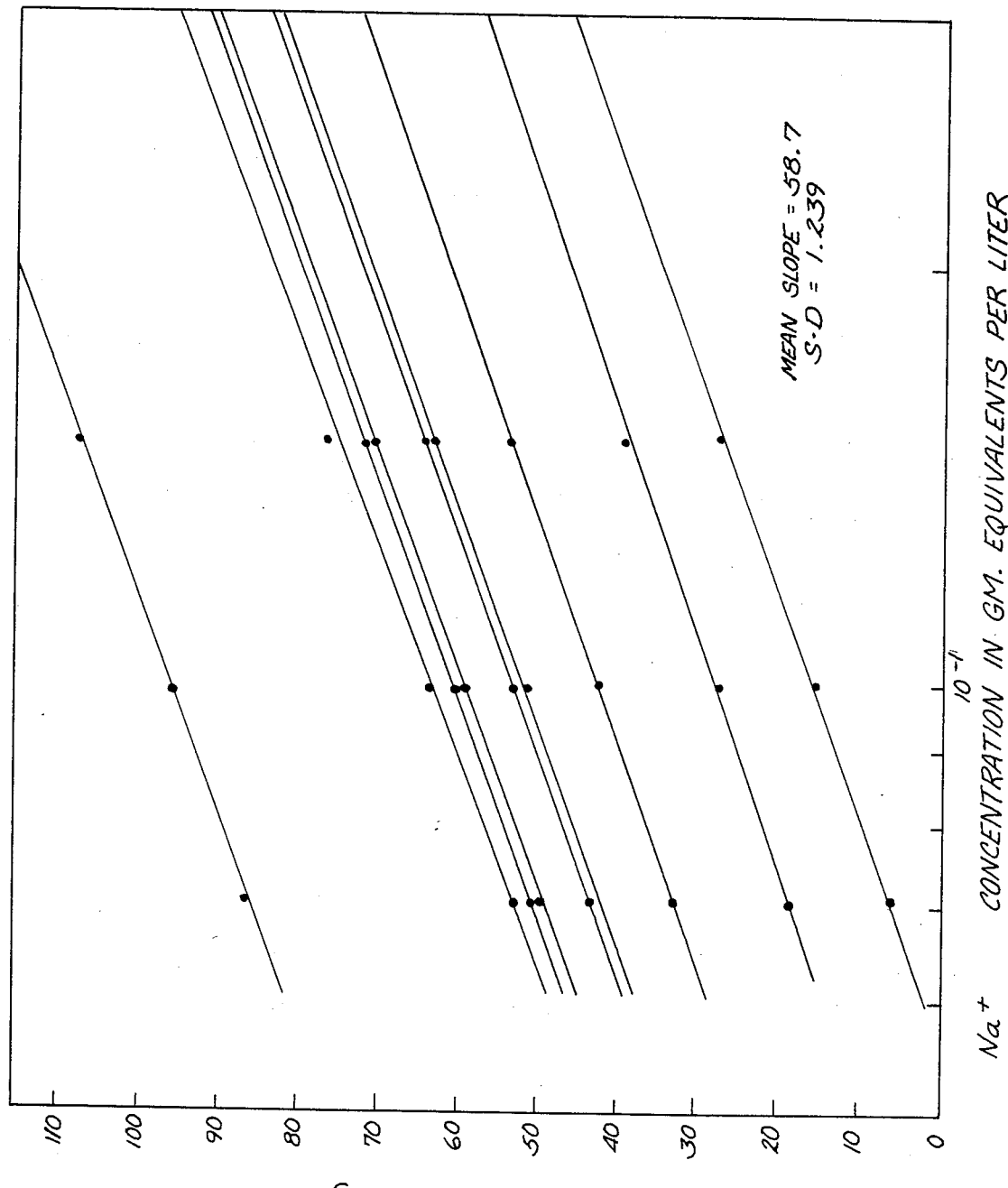
FIG. 5 is a graph showing the response of ISEs of the present invention having a sodium ionophore incorporated membrane to Na+ ions in the physiological range of blood.

The sodium ionophore incorporated membrane ISEs (Example 4) also exhibited excellent linearity and response in the physiological range of blood—see FIG. 5.

Figure 6:
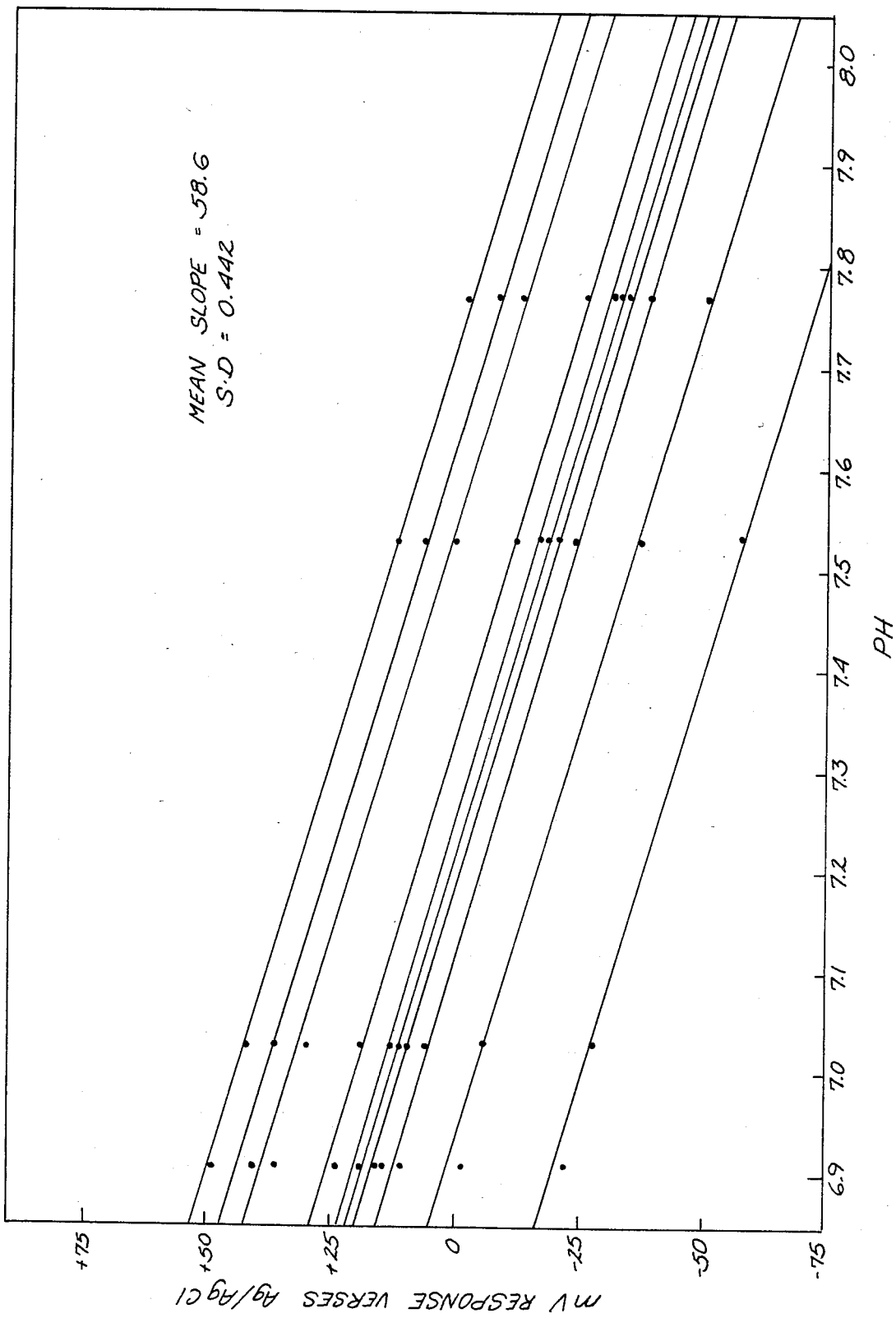
FIG. 6 is a graph showing the response of ISEs of the present invention having a tridodecylamine incorporated membrane to H+ ions in the physiological range of blood.

As shown in FIG. 6, the response of pH sensitive ISEs using a tridodecylamine incorporated membrane (Example 5) was found to be superior for the physiological pH range of blood (pH between about 6.5 and about 8.0). The constant value B was found to fall within a very narrow range from one ISE to another.

Figure 7:
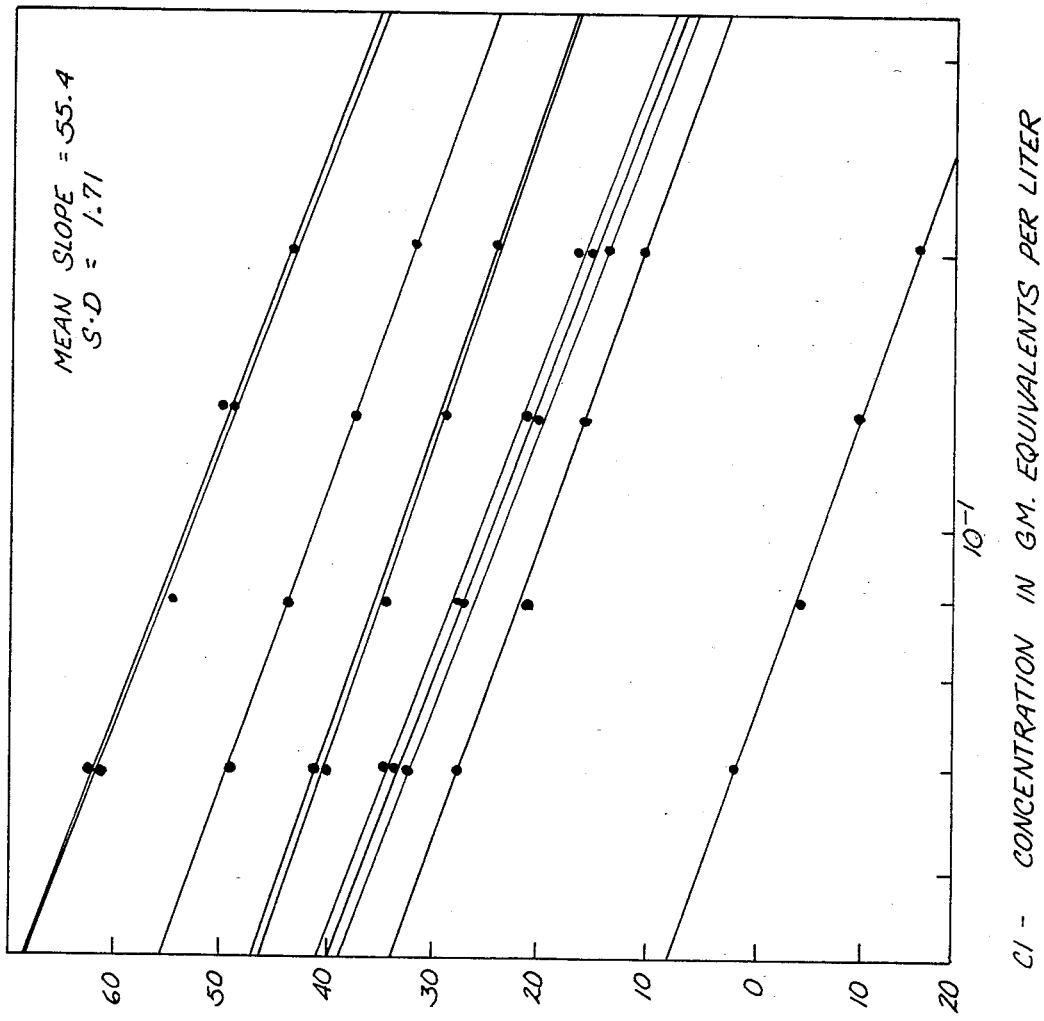
FIG. 7 is a graph showing the response of ISEs of the present invention having an Aliquat 336 incorporated membrane to Cl− in the physiological range of blood.

The chloride ion ISEs (Example 6) also showed good linearity over the range which was studied. See FIG. 7.

Figure 8:
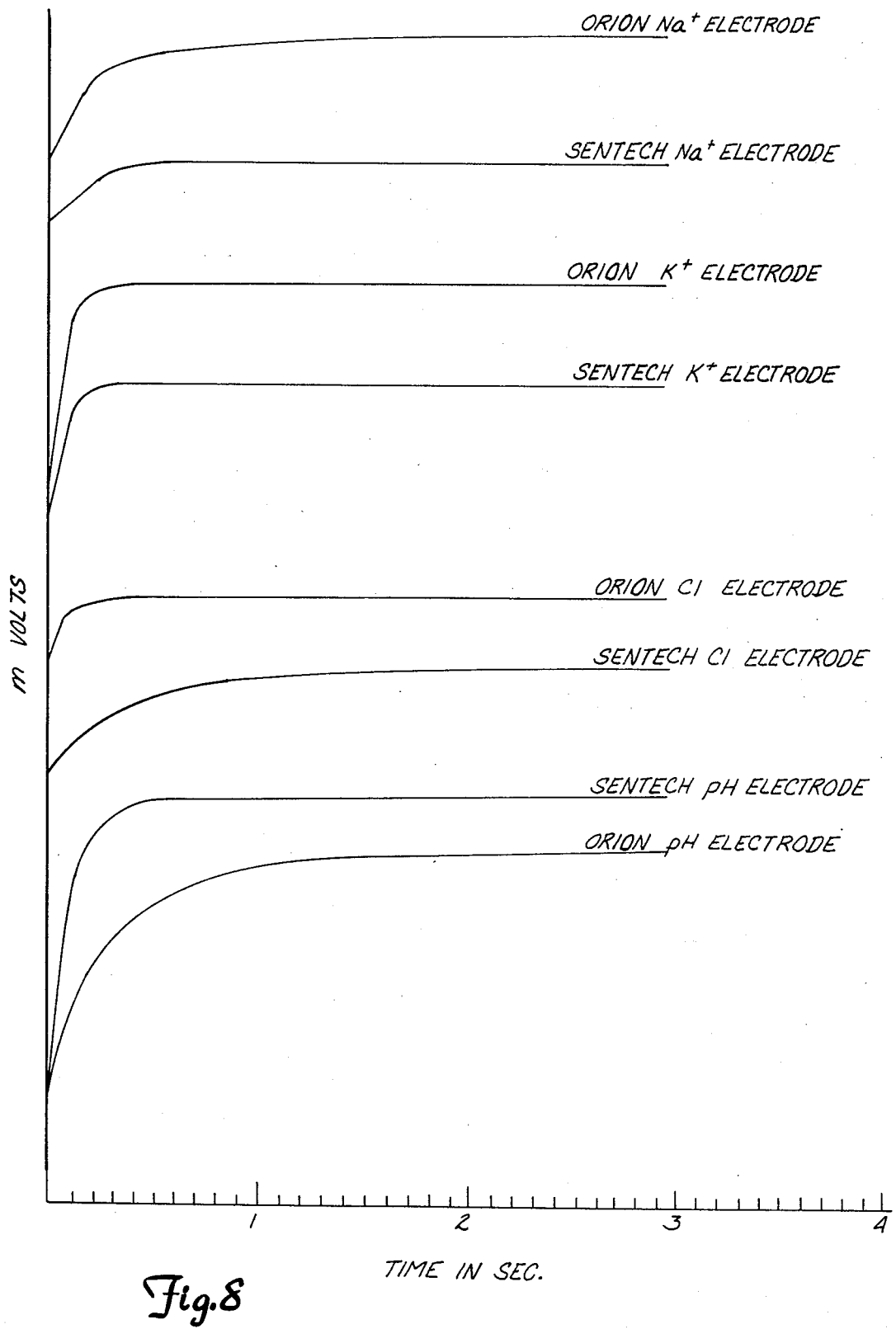
FIG. 8 is a graph comparing the response as a function of time of ISEs of the present invention and prior art ISEs.

The time responses of the ISEs of Example Nos. 1, 4, 5 and 6 were monitored on an oscilloscope screen and compared to the response of commercially available potassium, sodium, pH and chloride ISEs made by Orion Research, Inc. As shown in FIG. 8, the sodium, potassium and pH ISEs of the examples (labelled "Sen-Tech") exhibited comparable or faster response than the corresonding Orion ISEs. In the case of the chloride ISE, the response was slightly slower, but reached equilibrium in approximately one second.

It has been found that the shape of membrane 16, and the dimensional relationships between membrane 16 and electrode body 14 have a significant effect upon a response of ISE 10. In particular, it has been found that electrode body 14 must have an electrode surface area A1 which is smaller than the surface area A2 covered by membrane 16. Particuarly good results are obtained when the ratio of A1/A2 is between about 0.01 and about 0.25. Preferably, the ratio is about 0.16.

The height (thickness) of membrane 16 at its point above electrode surface 14A is also an important factor. ISEs having membrane heights or thicknesses less than about 0.5 mm tend to exhibit low slopes and high variability in the slope values. In addition, the failure rate of these ISEs tends to be high when the height of membrane 16 is less than about 0.5 mm.

Membrane heights in the range of 0.5 mm to about 0.9 mm are preferable, with a height of about 0.65 mm has proved very advantageous in achieving high Nernstian slope values, reproducibility of those slopes without using an excessive amount of membrane material.

The convex shape of membrane 14 allows for transport of the electroactive species to be more uniform across the active area of the electrode than other electrode configurations. For example, in experiments, applicants formed ISE structures in which the electrode body was located in a shallow well which had a greater diameter than the diameter of the electrode body. Although the membrane covered a greater surface area than just the surface area of the electrode body, the shape of the membrane was convex rather than concave. These ISEs exhibited low slopes, with high variability in slope value, and a high failure rate.

Figure 9A:
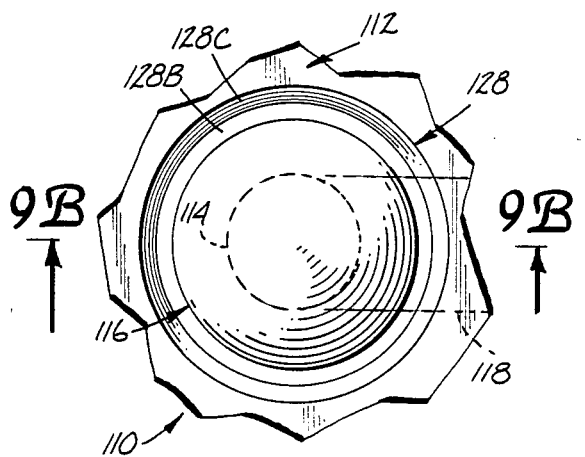
FIGS. 9A and 9B show top and cross-sectional views of a preferred embodiment of the ISE of the present invention used as a part of a disposable sensing device.
Figure 9B:
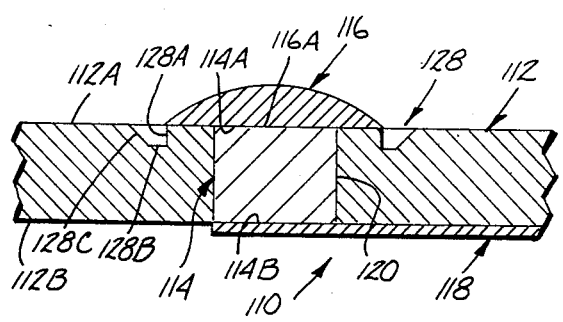

A particular advantage of the ISE of the present invention is its adaptability to a configuration useful in a disposable single-use device like the one described in the previously mentioned copending applications. FIGS. 9A and 9B show top and cross-sectional side views of ISE 110 which forms a part of a disposable single-use sensing card device. ISE 110 includes substrate 112, electrode body 114, species selective membrane 116 and conductor 118. In this particular embodiment, substrate 112 is an ABS plastic sheet which has a thickness of about 1.6 mm. Electrode body 114 is a solid graphite cylinder which has a diameter of 2.032 mm and which extends through hole 120 so that upper surfaces 112A and 114A and lower surfaces 112B and 114B are coplanar.

Conductor 118 runs over bottom surface 112B and makes contact with bottom surface 114B of electrode body 114. Conductor 118 provides the conductive path between the electrode body 114 and measurement circuitry of a clinical chemistry analyzer (not shown).

Moat 128 formed in upper surface 112A is concentrically arranged around electrode body 114 and defines the outer edge of membrane 116. Moat 128 has an essentially vertical inner shoulder 128A, an essentially horizontal bottom 128B, and a sloped outer shoulder 128C. The diameter of the inner edge of moat 128 is 3.556 mm, and the depth of moat 128 is about 0.381 mm. The inner diameter of sloped shoulder 128C is 4.064 mm, and the outer diameter of shoulder 128C is 4.826 mm. Shoulder 128C is sloped to accommodate the fow of calibrant and sample fluids, as they are introduced into a test chamber in which ISE 110 is located.

In conclusion, the present invention is an improved ion selective electrode which provides accurate response (i.e. Nernstian slopes), linear and reproducible slope values, and an extremely simple and low cost structure to manufacture.

Although the present invention has been described with reference to preferred embodiments, workers skilled in the art will recognize that changes may be made in form and detail without departing from the spirit and scope of the invention.

What is claimed is:

1. An ion selective electrode comprising:
   a conductive electrode body having an essentially planar first surface A1 with an outer edge;
   an insulating substrate supporting the electrode body and having an essentially planar first surface which surrounds and is essentially coplanar with the first surface of the electrode body; and
   a convex dome-shaped ion selective membrane over the first surfaces of the electrode body and the insulating substrate; the membrane covering an area A2 which is greater than the area of the first surface of the electrode body and the membrane having an outer edge which is spaced laterally from and which is essentially coplanar with the outer edge of the first surface of the electrode body.

2. The ion selective electrode of claim 1 wherein a ratio of area A1 of the first surface of the electrode body and area A2 covered by the membrane is between about 0.01 and about 0.25.

3. The ion selective electrode of claim 2 wherein the ratio A1/A2 is about 0.16.

4. The ion selective electrode of claim 1 wherein the membrane has a maximum thickness at a position over the first surface of the electrode body.

5. The ion selective electrode of claim 4 wherein the maximum thickness has an lower limit of about 0.5 mm.

6. The ion selective electrode of claim 5 wherein the maximum thickness has an upper limit of about 0.9 mm.

7. The ion selective electrode of claim 6 wherein the maximum thickness is about 0.65 mm.

8. The ion selective electrode of claim 1 wherein the electrode body has a second surface spaced from the first surface; and wherein the ion selective electrode further comprises means for making an electrical connection to the second surface of the electrode body.

9. The ion selective electrode of claim 8 wherein the substrate is a sheet having a second surface generally parallel to its first surface; and wherein the means for making an electrical connection comprises an electrical conductor which extends over a portion of the second surface of the substrate and contacts the second surface of the electrode body.

10. The ion selective electrode of claim 1 and further comprising a moat depression in the first surface of the substrate spaced from and surrounding the outer edge of the first surface of the electrode body.

11. The ion selective electrode of claim 10 wherein the outer edge of the membrane is defined by an inner edge of the moat depression.

12. The ion selective electrode of claim 11 wherein the moat depression in the first surface has an inner shoulder which extends downward from the inner edge of the moat and an outer shoulder which extends upward and outward to an outer edge of the moat.

13. The ion selective electrode of claim 1 wherein the membrane is a mixture of a polymer and an electroactive species.

14. The ion selective electrode of claim 1 wherein the electrode body is carbon.

15. The ion selective electrode of claim 1 wherein the first surface of the electrode body is a polished surface.

16. An ion selective electrode comprising:
a conductive electrode body having an essentially planar first surface;
an insulating substrate supporting the electrode body, the substrate having a first surface essentially coplanar with the first surface of the electrode body and having an annular moat depression surrounding and spaced from the electrode body; and
a convex dome-shaped ion selective membrane deposited over and directly in contact with the electrode body and the first surface of the substrate located within an area defined by an inner edge of the moat depression, the membrane having an outer edge which is spaced from an outer edge of the electrode body and which is defined by the inner edge of the moat.

17. A method of making an ion selective electrode comprising:
mounting a conductive electrode body in an insulating substrate so that the electrode body and the insulating substrate define an essentially planar surface with a moat depression in the insulating surface which surrounds and has an inner edge which is spaced laterally from an outer edge of the electrode body; and
depositing over the essentially planar surface a mixture of a polymer dispersed in plasticizer with an electroactive species dispersed therein to form a convex dome-shaped membrane over the essentially planar surface defined by the electrode body and a portion of the insulating substrate surrounding the electrode body, the membrane having an outer edge defined by the inner edge of the moat depression.

18. The method of claim 17 and further comprising: polishing the exposed surface of the electrode body prior to depositing.

19. An ion selective electrode comprising:
a conductive electrode having an essentially planar first surface with an area A1;
an insulating substrate supporting the electrode body and having an essentially planar first surface which surrounds and is essentially coplanar with the first surface of the electrode body; and
a convex dome-shaped ion selective membrane over the first surfaces of the electrode body and the insulating substrate; the membrane having a maximum thickness at a position over the first surface of the electrode body which is between about 0.5 mm and about 0.9 mm; and the membrane covering an area A2 which is greater than area A1 of the first surface of the electrode body and having an outer edge which is generally concentrically spaced from and coplanar with an outer edge of the first surface of the electrode body, wherein A1/A2 is between about 0.01 and about 0.25.

20. The ion selective electrode of claim 19 and further comprising a moat depression in the first surface of the substrate having an inner edge spaced laterally from and surrounding the outer edge of the first surface of the electrode body, and wherein the outer edge of the membrane is defined by an inner edge of the moat.

21. An ion selective electrode comprising:
a conductive electrode body having an essentially planar surface;
an insulating substrate supporting the electrode body, the substrate having a surface essentially coplanar with and surrounding the planar surface of the electrode body and having an annular moat depression generally concentrically positioned to surround the electrode body with an inner edge of the moat depression spaced from an outer edge of the electrode body; and
a convex dome ion selective membrane deposited over and directly in contact with the electrode body and a surface of the substrate within the moat.

22. A method of making an ion selective electrode comprising:
mounting a conductive electrode body in an insulating substrate so that the electrode body and the insulating substrate form an essentially planar exposed surface surrounded generally concentrically by a moat depression; and
depositing over the planar exposed surface a mixture of a polymer dispersed in plasticizer with an electroactive species dispersed therein to form, as a result of surface tension, a convex dome-shaped membrane over the electrode body and the portion of the insulating substrate surrounding the electrode body, the membrane having an outer edge defined by an inner edge of the moat depression.

* * * * *